US007998075B2

(12) United States Patent
Ragauskas et al.

(10) Patent No.: US 7,998,075 B2
(45) Date of Patent: Aug. 16, 2011

(54) APPARATUS AND METHOD OF NON-INVASIVE CEREBROVASCULAR AUTOREGULATION MONITORING

(75) Inventors: Arminas Ragauskas, Kaunas (LT);
Gediminas Daubaris, Kaunas (LT);
Vytautas Petkus, Kaunas (LT);
Renaidas Raisutis, Kaunas (LT)

(73) Assignee: UAB Vittamed Technologijos (LT)

( * ) Notice: Subject to any disclaimer, the term of this patent is extended or adjusted under 35 U.S.C. 154(b) by 686 days.

(21) Appl. No.: 12/109,873

(22) Filed: Apr. 25, 2008

(65) Prior Publication Data
US 2009/0270734 A1    Oct. 29, 2009

(51) Int. Cl.
*A61B 8/06* (2006.01)
(52) U.S. Cl. .................................. 600/448; 600/438
(58) Field of Classification Search .................. 600/311, 600/340, 344, 358, 363, 364, 372, 390, 438, 600/454, 459, 465, 480, 484–488, 504, 533, 600/534, 544
See application file for complete search history.

(56) References Cited

U.S. PATENT DOCUMENTS
5,388,583 A    2/1995   Ragauskas et al.
6,387,051 B1   5/2002   Ragauskas et al.

FOREIGN PATENT DOCUMENTS
CN   1883383 A    12/2006
RU   2195860 C2    1/2003
WO   2006050078 A2    5/2006

OTHER PUBLICATIONS

Fountas et al. Is non-invasive monitoring of intracranial pressure waveform analysis possible? Preliminary results of a comparative study of non-invasive vs. invasive intracranial slow-wave waveform analysis monitoring in patients with traumatic brain injury. Med. Sci Moni. Feb. 2005 11(2): CR58-63. Abstract only.*
Schmidt, Bernhard, et al, "Adaptive Noninvasive Assessment of Intracranial Pressure and Cerebral Autoregulation" Journal of the American Heart Association, pp. 84-89, Dec. 12, 2002.
Panerai, Ronney B, "Assessment of cerebral pressure autoregulation in humans—a review of measurement methods" Physiol. Meas., pp. 305-338, 1998.
Aaslid, R., et al "Cerbral autoregulation dynamics in humans", The Journal of the American Heart Association, pp. 45-52, 1989.
Ragauskas, A., et al, "Clincial study of continuous non-invasive cerebrovascular autoregulation monitoring in neurosurgical ICU" Acta Neurochir, pp. 367-370, 2005.

(Continued)

*Primary Examiner* — Parikha S Mehta
(74) *Attorney, Agent, or Firm* — St. Onge Steward Johnston & Reens LLC

(57) ABSTRACT

A non-invasive method for monitoring of cerebrovascular blood flow autoregulation state includes sensing intracranial blood volume waves, filtering a slow wave, respiratory wave, and pulse wave informative components from said intracranial blood volume waves, filtering slow wave and respiratory wave reference components from the pulse wave envelope, calculating a first phase shift between said slow wave informative component and said slow wave reference component, calculating a second phase shift between said respiratory wave informative component and said respiratory wave reference component, and calculating the index of evaluation of the status of cerebral autoregulation state (ICAS) from said first phase shift and said second phase shift.

21 Claims, 7 Drawing Sheets

OTHER PUBLICATIONS

Czosnyka, Marek PhD, et al "Continuous Assessment of the Cerebral Vasomotor Reactivity in Head Injury" Neurosurgery Online, pp. 11-19, Jul. 1997.

Schondort, Ronald, et al, "Dynamic cerebral autoregulation is preserved in neurally mediated syncope" J Appl Physiol, pp. 2493-2502, 2001.

Panerai, Ronney B., et al, "Linear and nonlinear analysis of human dynamic cerebral autoregulation", Am J Phsyiol Heart Circ, H1089-H1099, 1999.

Latka, Miroslaw, et al, "Phase dynamics in cerebral autoregulation" Am J Physiol Heart Circ, pp. H2272-H2279, 2005.

Paneria, Ronney B., et al, "Short-Term Variability of Cerebral Blood Flow Velocity Response to Arterial Blood Pressure Transients", Ultrasound in Med. & Bio., pp. 31-38, 2003.

Ronney B Panerai: "Cerebral Autoregulation: From Models to Clinical Applications" Cardiovascular Engineering: An International Journal, Kluwer Academic Publishers—Plenum Publishers, NE, vol. 8, No. I, Nov. 28, 2007, pp. 42-59, XP019570714 ISSN: 1573-6806.

European Search Report; EP 09 15 8708; Aug. 12, 2009; 4 pages.

* cited by examiner

APPARATUS AND METHOD OF NON-INVASIVE CEREBROVASCULAR AUTOREGULATION MONITORING

FIELD OF THE INVENTION

The present invention relates to a method and apparatus for the non-invasive measurement and monitoring of cerebrovascular autoregulation state.

BACKGROUND OF THE INVENTION

Autoregulation is the intrinsic tendency of the body to keep blood flow constant when blood pressure varies. In the brain, cerebral blood vessels are able to regulate the flow of blood through them by altering their diameters—they constrict when systemic blood pressure is raised and dilate when it is lowered. Cerebral blood flow autoregulation has been shown to be affected by a number of important clinical conditions such as premature birth, birth asphyxia, stroke, head injury, carotid artery disease, hypertension and vasovagal syncope. Acute cerebral diseases (e.g., traumatic brain injury, stroke) frequently lead to a rise in intracranial pressure (ICP) and impairment of cerebral autoregulation (see Aaslid R. et al., 1989, Cerebral autoregulation dynamics in humans, *Stroke*, 20:45-52; Czosnyka M. et al., 1997, Continuous assessment of the cerebral vasomotor reactivity in head injury, *Neurosurgery*, 41:11-19; Panerai R. B., 1998, Assessment of cerebral pressure autoregulation in humans-a review of measurement methods, *Physiol. Meas.*, 19:305-338; and Schondorf R. et al., 2001, Dynamic cerebral autoregulation is preserved in neurally mediated syncope, *J. Appl. Physiol.*, 91:2493-2502).

Assessment of cerebrovascular autoregulation state (CAS) could be of vital importance in ensuring the efficacy of therapeutic measures in the case of brain injury and stroke. Continuous monitoring of CAS and CAS monitoring data based treatment of intensive care patients with brain injuries or stroke will reduce mortality and morbidity of such patients.

Various methods have previously been introduced to assess CAS (see Aaslid R. et al. (1989), 20:45-52; Panerai R. B. (1998), 19:305-338). These discrete clinical tests, like the cuff leg test (see Aaslid R. et al. (1989), 20:45-52), however, did not provide continuous monitoring data about CAS. There is a need for continuous real-time CAS monitoring because it is the optimal monitoring for use with CAS based therapy.

A few methods and techniques have been proposed for invasive, semi non-invasive, and non-invasive monitoring of CAS (see Czosnyka M et al. (1997), 41:11-19; Schmidt B et al., 2003, Adaptive noninvasive assessment of intracranial pressure and cerebral autoregulation, *Stroke*, 43:84-89). These methods are based on the estimation of the correlation factor between arterial blood pressure (ABP) and ICP slow waves or ABP and cerebral blood flow velocity (CBFV) slow waves (see Czosnyka M et al. (1997), 41:11-19; Schmidt B et al. (2003), 43:84-89). In the case of intact cerebrovascular autoregulation, the correlation factor between ABP and ICP slow waves is negative and close to −1.0. In the case of impaired CAS the same factor is positive and close to +1.0.

The disadvantages of slow invasive or non-invasive ABP and ICP wave correlation monitoring methods include but are not limited to the following. First, slow ICP waves are not permanent and their amplitude is too low (less than 3.0 mmHg during main part of ICU patients' continuous monitoring time) to measure with sufficient accuracy. Also, non-invasive measurement or prediction of slow ICP waves adds additional errors and distortions of such waves. Further, if invasive slow ICP wave measurement is replaced by non-invasive transcranial Doppler (TCD) CBFV measurement, additional errors and distortions of such waves will occur. Moreover, slow ABP waves are also sometimes too small to measure with sufficient accuracy and non-invasively.

Also, the period of slow ICP or ABP waves is estimated to be from approximately 30 seconds to 120 seconds or more. In order to evaluate the CAS applying the intermittent slow wave method, it is necessary to accumulate the measured data during 4.0 minutes or longer. This is a relatively long time period and thus becomes a long term process. Long time period testing of CAS is not always effective because variability of CAS is a short-term process (see Panerai R B et al., 2003, Short-term variability of cerebral blood flow velocity responses to arterial blood pressure transients, *Ultrasound in Med. & Biol.*, 29:1:31-38). Because of this time delay of prior art CAS monitoring systems, secondary brain injury can take place in ICU coma patients before the CAS monitoring data becomes available. The time delay of the slow wave CAS monitoring method is therefore too long for clinical practice of ICU patients monitoring and CAS based treatment.

Additionally, cerebrovascular autoregulation is a complex, nonlinear, and multivariate mechanism with considerable short-term variability (see Panerai R. B. et al. (2003), 29:1:31-38). A correlation factor can be applied without problems as an indicator of CAS only in linear autoregulatory systems. However, because the cerebrovascular autoregulation system is nonlinear (see Panerai R. B. et al., 1999, Linear and nonlinear analysis of human dynamic cerebral autoregulation, *Am. J. Physiol.*, 277:1089-1099), any correlation factor between a reference signal (ABP slow wave) and a nonlinearly distorted cerebrovascular autoregulation system output signal (ICP or CBFV slow wave) would be a questionable indicator of CAS.

In our previous art (A. Ragauskas et al WO2006/050078), we presented a method for continuous real-time CAS monitoring based on simultaneous, non-invasive monitoring of intracranial blood volume respiratory waves (or other intracraniospinal characteristics related to the respiration processes) and lung volume respiratory waves (or other extracranial physiological characteristics related to the lung respiration processes). Intracranial blood volume respiratory waves and lung volume respiratory waves were filtered or decomposed in real-time into narrowband sinewave first harmonic components, and the phase shift between intracranial blood volume respiratory wave and lung volume respiratory wave first harmonics' was determined therefrom. Cerebrovascular autoregulation state (CAS) was derived from that phase shift value.

The method was based on the following assumptions:
If the phase difference between non-invasively measured intracranial blood volume respiratory waves and lung volume respiratory waves is close to zero, cerebrovascular autoregulation is impaired.
If the phase difference between intracranial blood volume respiratory waves and lung volume respiratory waves is equal or more than 30 to 40 degrees, cerebrovascular autoregulation is intact.
Phase difference reflects the severity of impairment of CAS. The smaller the phase difference, the greater the severity of impairment. The threshold value of 30 degrees divides the severity into intact CAS and impaired CAS.

Similar results of phase shift dependence on frequency in the cases of intact CAS was obtained by M. Latka et. al (M. Latka, M. Turalska, M. Glaubic-Latka, W. Kolodziej, D.

Latka, B. J. West, 2005, Phase dynamics in cerebral autoregulation, *Am J Physiol Heart Circ Physiol*, 289:2272-2279).

The disadvantages of the method described in WO2006/050078 to Ragauskas et al. are:

Sensitivity of the method is dependent on the frequency of the cerebral blood volume waves and respiratory waves. As shown in FIG. 7, this sensitivity decreases when frequency of respiration increases (see A. Ragauskas et al., 2005, Clinical study of continuous non-invasive cerebrovascular autoregulation monitoring in neurosurgical ICU, *Acta Neurochir*, Supp. 95:367-370).

In order to implement this method, it is necessary to use a respiratory sensor (lung volume sensor), which generates additional errors of phase shift. This error is dependent on the sensor's mounting position and patient respiration behavior.

In the CAS evaluation methods which use ABP waves (slow waves or respiratory) it is necessary apply an invasive ABP sensor. Disadvantages of the use of invasive ABP sensor are:

implantation of ABP sensor in artery is a complex and risky procedure;

it necessary to replace ABP sensor periodically in order to avoid mortification of body parts; and the use of invasive sensors is prohibitive of applying the method to healthy volunteers or to the patients with moderate or mild brain injuries or other brain pathologies not connected with injuries.

Accordingly, it is an object of the present invention to provide a method and apparatus for continuous real-time CAS monitoring that solve the problems and cures the deficiencies of the prior art methods, apparatuses and techniques.

The present invention, which is a further development of the previous invention WO2006/050078 to Ragauskas et al., provides a non-invasive ultrasonic method and apparatus of CAS monitoring, which is based on the application of the following non-invasively monitored intracranial or cerebral blood volume (IBV) waves:

informative IBV slow waves, which phase shift due to human cerebrovascular autoregulatory mechanism has the highest sensitivity to CAS as shown in FIG. 7;

informative IBV respiratory waves, which phase shift due to human cerebrovascular autoregulatory mechanism also has sensitivity to CAS as shown in FIG. 7; and reference pulse waves, which amplitude is modulated by intracranial slow and respiratory waves and which envelope contains slow waves and respiratory waves not affected by the cerebrovascular autoregulatory mechanism (CVA).

We found experimentally during clinical studies of patients with traumatic brain injuries that the intracranial slow and respiratory waves extracted from the envelope of the intracranial pulse waves are not affected by human CVA. These waves are not informative, but they can be used as reference waves in comparison with informative slow and respiratory waves. Therefore, it is no longer necessary to use invasive or non-invasive extracranial ABP or respiratory wave sensors in order to get the reference waves for CVA status evaluation.

The phase shift between intracranial informative IBV slow waves and reference slow waves extracted from the IBV pulse wave envelope, as well as the phase shift between intracranial informative IBV respiratory waves and reference respiratory waves obtained from the pulse wave envelope give information about the human CAS. The simultaneous application of intracranial blood volume waves obtained from wide frequency range (respiratory waves and slow waves) allows us to increase the reliability of the real-time monitoring information about human CAS status.

SUMMARY OF THE INVENTION

Accordingly, it is an object of the present invention to provide a non-invasive method and apparatus for continuous real-time CAS monitoring.

It is a further object of the present invention to provide a method and apparatus for CAS monitoring that does not require the use of additional external sensors for the measurement of lung volume respiratory reference waves.

It is yet a further object of the present invention to provide a method and apparatus for CAS monitoring that does not rely on the measurement of arterial blood pressure (ABP) and intracranial pressure (ICP) slow waves to determine CAS.

In order to overcome the deficiencies of the prior art and to achieve at least some of the objects and advantages listed, an embodiment of the method for non-invasively monitoring cerebrovascular autoregulation state includes obtaining intracranial blood volume waves, filtering a first informative wave from the intracranial blood volume waves, filtering a second informative wave from the intracranial blood volume waves, filtering a primary reference wave from the intracranial blood volume waves, demodulating the primary reference wave into a reference wave envelope, filtering a first reference wave from the reference wave envelope, filtering a second reference wave from the reference wave envelope, calculating a first phase shift between said first informative wave and said first reference wave, calculating a second phase shift between said second informative wave and said second reference wave, calculating an index of evaluation of the status of cerebral autoregulation state from said first phase shift and said second phase shift, and comparing said index of evaluation of the status of cerebral autoregulation state to a predetermined index threshold value to determine cerebrovascular autoregulation state.

The first informative wave may comprise intracranial blood volume slow waves, the second information wave may comprise intracranial blood volume respiratory waves, and the primary reference wave may comprise intracranial blood volume pulse waves. The first reference wave may comprise slow waves from the pulse wave envelope and the second reference wave may comprise respiratory waves from the pulse wave envelope.

The index of evaluation of the status of cerebrovascular autoregulation state may be calculated using the following formula:

$$ICAS = \cos(\pi - a1 * PS1 - a2 * PS2)$$

where PS1 is the first phase shift and PS2 is the second phase shift and where a1 and a2 are weighting factors. The value of weighting factor a1 is most preferably 0.61 and the value of weighting factor a2 is most preferably 0.42. However, other weighting factors may be used. If the calculated ICAS is close to −1.0, cerebrovascular autoregulation state is absolutely intact. If the calculated ICAS is close to +1.0, cerebrovascular autoregulation state is absolutely impaired.

In an additional embodiment, the method for non-invasively monitoring cerebrovascular autoregulation state includes non-invasively obtaining intracranial blood volume waves, filtering a slow wave informative component from said intracranial blood volume waves, filtering a respiratory wave informative component from said intracranial blood volume waves, filtering a pulse wave component from said intracranial blood volume waves, demodulating said pulse wave component into a pulse wave envelope, filtering a slow wave reference component from the pulse wave envelope, filtering a respiratory wave reference component from the pulse wave envelope, calculating a first phase shift between said slow wave informative component and said slow wave reference component, calculating a second phase shift between said respiratory wave informative component and said respiratory wave reference component, calculating the index of evaluation of the status of cerebral autoregulation state from said first phase shift and said second phase shift, and comparing said index of evaluation of the status of cerebral autoregulation state to a predetermined index threshold value to determine cerebrovascular autoregulation state.

An embodiment of an apparatus for non-invasively monitoring cerebrovascular autoregulation state is also provided. The apparatus includes a device for obtaining intracranial blood volume waves and generating a blood volume output signal; a first slow wave filter connected to said device for receiving the blood volume output signal, filtering the blood volume output signal, and generating a slow wave informative signal; a second respiratory wave filter connected to said device for receiving the blood volume output signal, filtering the blood volume output signal, and generating a respiratory wave informative signal; and a pulse wave filter connected to said device for receiving the blood volume output signal, filtering the blood volume output signal, and generating a pulse wave reference signal. The device may be a non-invasive measurement device, more specifically, it may be an ultrasonic "time-of-flight" measurement device.

An envelope detector is connected to the pulse wave filter for receiving the pulse wave reference signal, for demodulating said pulse wave reference signal into a pulse wave envelope, and generating a pulse wave envelope signal. A second slow wave filter is connected to the envelope detector for receiving the pulse wave envelope signal, filtering the pulse wave envelope signal, and generating a slow wave reference signal. In addition, a second respiratory wave filter is also connected to the envelope detector for receiving the pulse wave envelope signal, filtering the pulse wave envelope signal, and generating a respiratory wave reference signal.

A first phase shift monitor is connected to the first slow wave filter for receiving the slow wave informative signal and the second slow wave filter for receiving the slow wave reference signal. The first phase shift monitor then determines the phase shift between the slow wave informative signal and the slow wave reference signal and generates a first phase shift value output. A second phase shift monitor is connected to the first respiratory wave filter for receiving the respiratory wave informative signal and the second respiratory wave filter for receiving the respiratory wave reference signal. The second phase shift monitor then determines the phase shift between the respiratory wave informative signal and the respiratory wave reference signal and generates a second phase shift value output.

Last, a processor receives the first phase shift value output from the first phase shift monitor and the second phase shift value output from the second phase shift monitor, calculates an index of evaluation of the status of cerebral autoregulation state, and compares said index of evaluation of the status of cerebral autoregulation state value with a stored predetermined index threshold value to determine the status of cerebrovascular autoregulation state.

The first slow wave filter and the second slow wave filter may comprise a bandpass filter having a bandwidth of approximately 0.008 Hz to 0.033 Hz. The first respiratory wave filter and the second respiratory wave filter may comprise a bandpass filter having a bandwidth of approximately 0.1 Hz to 0.35 Hz. The pulse wave filter may comprise an adaptive bandpass filter having a bandwidth ranging from approximately the frequency of the first harmonic of the pulse waves to the frequency of the fifth harmonic of the pulse waves.

DETAILED DESCRIPTION OF THE INVENTION

Figure 1:
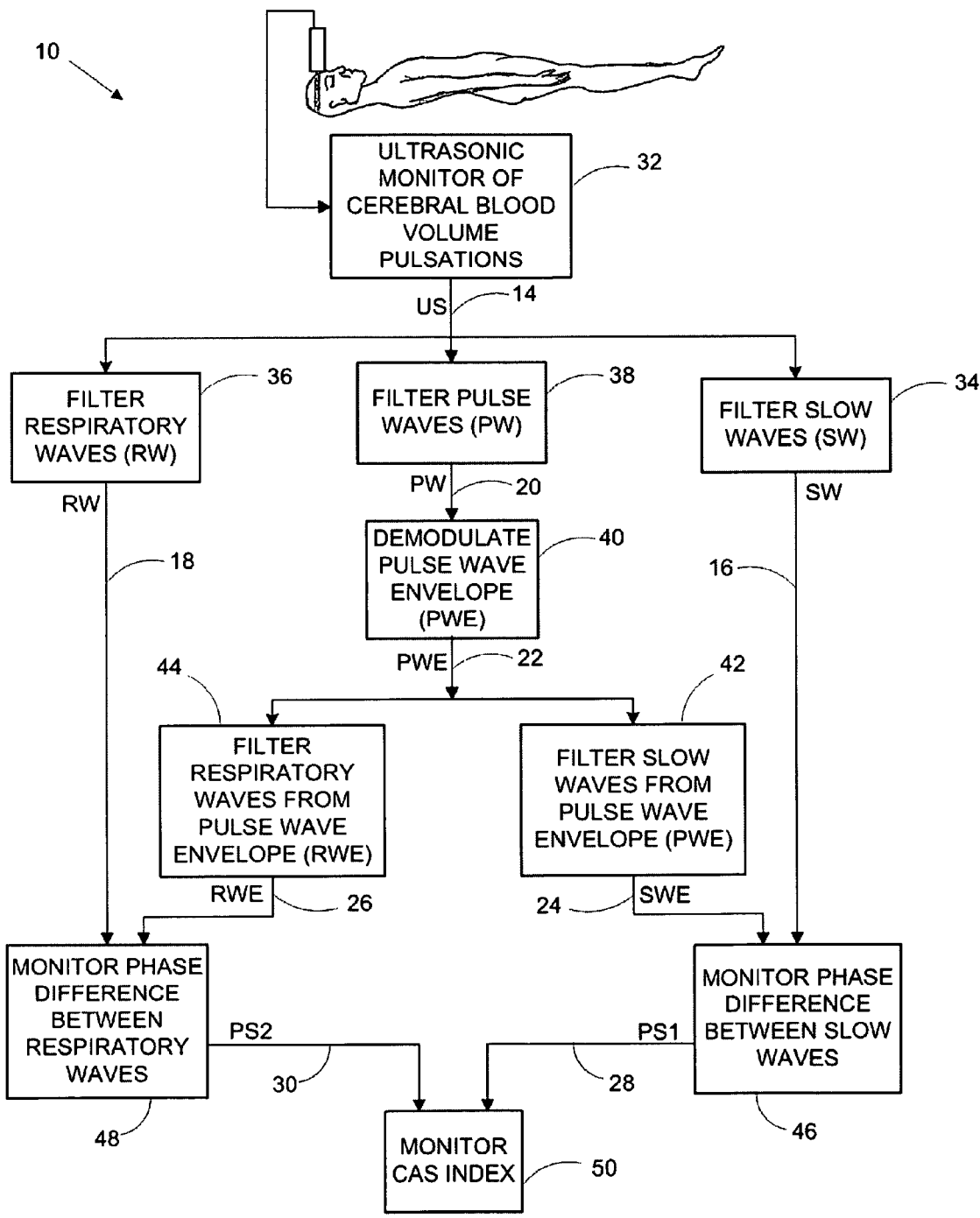
FIG. 1 is a block diagram depicting an example of the method of the present invention.
Figure 2:
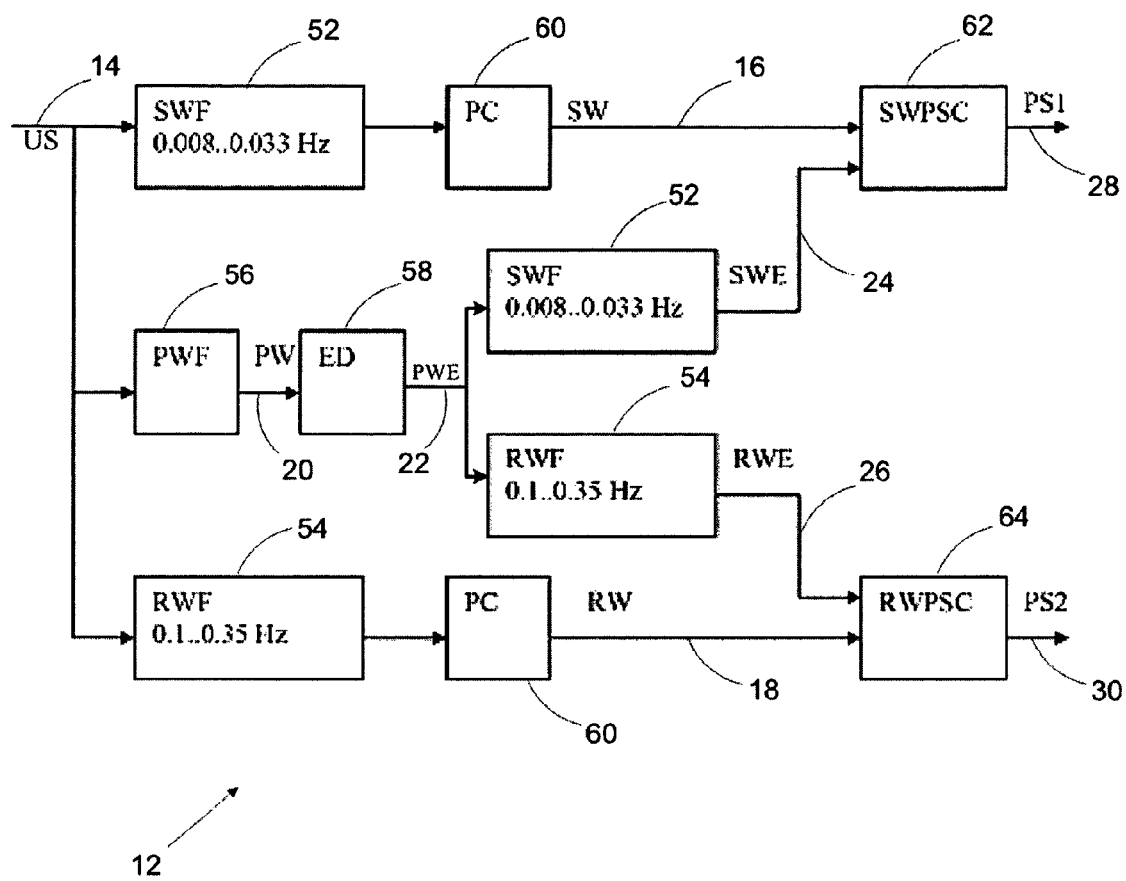
FIG. 2 is a block diagram of an embodiment of the apparatus of the present invention.

The cerebrovascular autoregulation (CA) monitoring method 10 of the present invention is based on the non-invasive measurement of cerebral blood volume waves within brain parenchyma using an ultrasonic "time-of-flight" measurement device 32. As shown in FIGS. 1 and 2, this device 32 is capable of obtaining ultrasound speed inside the brain parenchymal acoustic path. Ultrasound speed directly reflects cerebral blood volume waves: slow waves, respiratory waves and pulse waves. This "time-of-flight" measurement device 32 is described in detail in U.S. Pat. Nos. 5,388,583 and 6,387,051, both to Ragauskas. It is understood by those of skill in the art that other devices may be used to obtain the cerebral blood volume waves.

As used in FIGS. 1 and 2, signal US 14 is a non-invasively measured relative ultrasound speed variation within brain parenchyma acoustic path, which reflects cerebral blood volume waves; signal SW 16 is filtered slow waves; signal RW 18 is filtered respiratory waves; signal PW 20 is filtered pulse waves (up to 5 harmonics); signal PWE 22 is an envelope of filtered pulse waves; signal SWE 24 is filtered slow waves from pulse wave envelope; and signal RWE 26 is filtered respiratory waves from pulse wave envelope. PS1 is the phase difference between signal SW 16 and signal SWE 24. PS2 is the phase difference between signal RW 18 and signal RWE 26.

FIG. 1 includes a block diagram of an embodiment of the innovative non-invasive method 10 for monitoring cerebrovascular autoregulation. This embodiment of method 10 performs the following mathematical processing in order to get quantitative information about the status of human cerebrovascular autoregulation state (CAS):

noninvasively monitor cerebral blood volume pulsations at 32;

filter slow waves (SW) using slow waves band-pass filters (SWF) (from frequency range 0.008 Hz to 0.033 Hz) at 34, filter respiratory waves (RW) using respiratory wave band-pass filters (RWF) (from frequency range 0.1 Hz to 0.35 Hz) at 36, filter pulse waves (PW) using pulse wave band-pass filters PWF (up to 5 harmonics of pulse waves) at 38, demodulate pulse wave envelope (PWE) using envelope detector (ED) at 40, extract (filter) slow waves from pulse wave envelope (SWE) using mentioned above slow waves band-pass filters SWF at 42, extract (filter) respiratory waves from pulse wave envelope (RWE) using mentioned above respiratory waves band-pass filters RWF at 44, calculate phase shift (PS1) between slow waves SW and SWE at 46, calculate phase shift (PS2) between respiratory waves RW and RWE at 48, and calculate the index of evaluation cerebrovascular autoregulation from the obtained values of phase shifts PS1 and PS2 at 50.

FIG. 2 includes a block diagram of an embodiment of the innovative non-invasive apparatus 12 for monitoring cerebrovascular autoregulation. SWF 52 is a band-pass filter used for filtering of slow waves and preferably has a bandwidth of 0.008 Hz to 0.033 Hz, which corresponds to a typical range of physiological slow B waves. Two identical SWFs 52 are used for data mathematical processing—one for filtering slow waves SW 16, and another for filtering slow waves from the pulse wave envelope SWE 24. RWF 54 is a band-pass filter used for filtering of respiratory waves and preferably has a bandwidth of 0.1 Hz to 0.35 Hz, which corresponds to a typical range of physiological respiration. The bandwidth of the filters may be optimally adjusted to correspond to the real respiratory period of each human. Two identical RWFs 54 are used for data mathematical processing—one for filtering respiratory waves RW 18, and another for filtering respiratory waves from the pulse wave envelope RWE 26. PWF 56 is a band-pass filter used for filtering of pulse waves 20 and has a bandwidth that must be adjusted individually to each human heart rate and must cover a frequency range from the 1st harmonic up to the 5th harmonic of the pulse wave. ED 58 is an envelope detector, which is used to obtain envelope from the filtered pulse waves PWE 22. PC 60 is a phase corrector, which is used to compensate for the delay of pulse wave filter PWF 56. Two phase correctors 60 are used in the diagram, one for PWF delay compensation in slow waves channel, and another for PWF delay compensation in respiratory wave channels.

SWPSC 62 is a calculator of phase shift between slow waves SW 16 and SWE 24. The output of the calculator is a calculated phase shift PS1 (28). RWPSC 64 is a calculator of phase shift between respiratory waves RW 18 and RWE 26. The output of the calculator is a calculated phase shift PS2 (30). The obtained phase shifts PS1 (28) and PS2 (30) directly give information about the status of cerebral autoregulation, and therefore are used to calculate the index of evaluation of the status of CAS (ICAS):

$$ICAS = \cos(\pi - a1*PS1 - a2*PS2); \text{ or } ICAS = f(PS1; PS2)$$

Where a1 and a2 are weighting factors. The value of weighting factor a1 is most preferably 0.61 and the value of weighting factor a2 is most preferably 0.42, however, other weighting factors may be used. These preferable values were found during the clinical study on brain injured patients discussed below.

The range of the ICAS is from −1.0 to +1.0. For the cases of the absolutely intact cerebral autoregulation the value of ICAS is close to −1.0, in the cases of absolutely impaired autoregulation the value of ICAS is close to +1.0.

To test the apparatus and method of the present invention, seven traumatic brain injury patients in different pathophysiological states were monitored simultaneously invasively and non-invasively using an invasive ICP monitor (Codman or Camino), an invasive ABP monitor (Datex), and a non-invasive time of-flight monitor (Vittamed).

The monitoring data from the invasive ICP monitor and invasive ABP monitor where processed in order to get slow ICP and slow ABP waves (in the frequency range 0.008 Hz to 0.033 Hz). These slow waves were used to calculate moving correlation coefficient r(ICP; ABP) which has been taken as an index of CAS status estimation:

$$ICAS(invasive) = r(ICP; ABP)$$

The monitoring data from the non-invasive time of-flight monitor (relative ultrasound speed) was processed in order to get slow waves, respiratory waves, and pulse waves and to calculate phase shifts PS1 and PS2. These phase shifts were used to calculate non-invasive index of CAS status estimation:

$$ICAS(non\text{-}invasive) = \cos(\pi - a1*PS1 - a2*PS2); \text{ or } ICAS = f(PS1; PS2)$$

Figure 3:
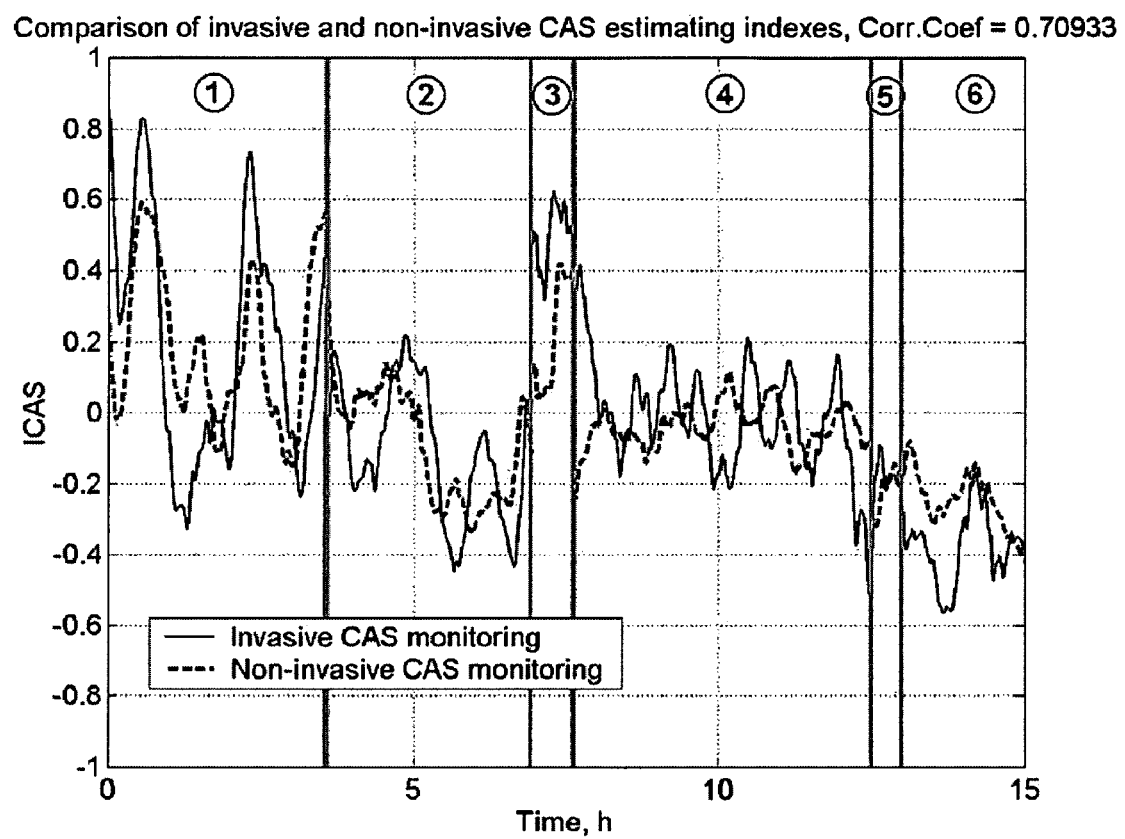
FIG. 3 is a chart showing display results of invasive and non-invasive CAS monitoring using slow and respiratory waves together according to the proposed method of the present invention. The non-invasive ICAS clinical data was collected and processed using the method of the present invention.
Figure 4:
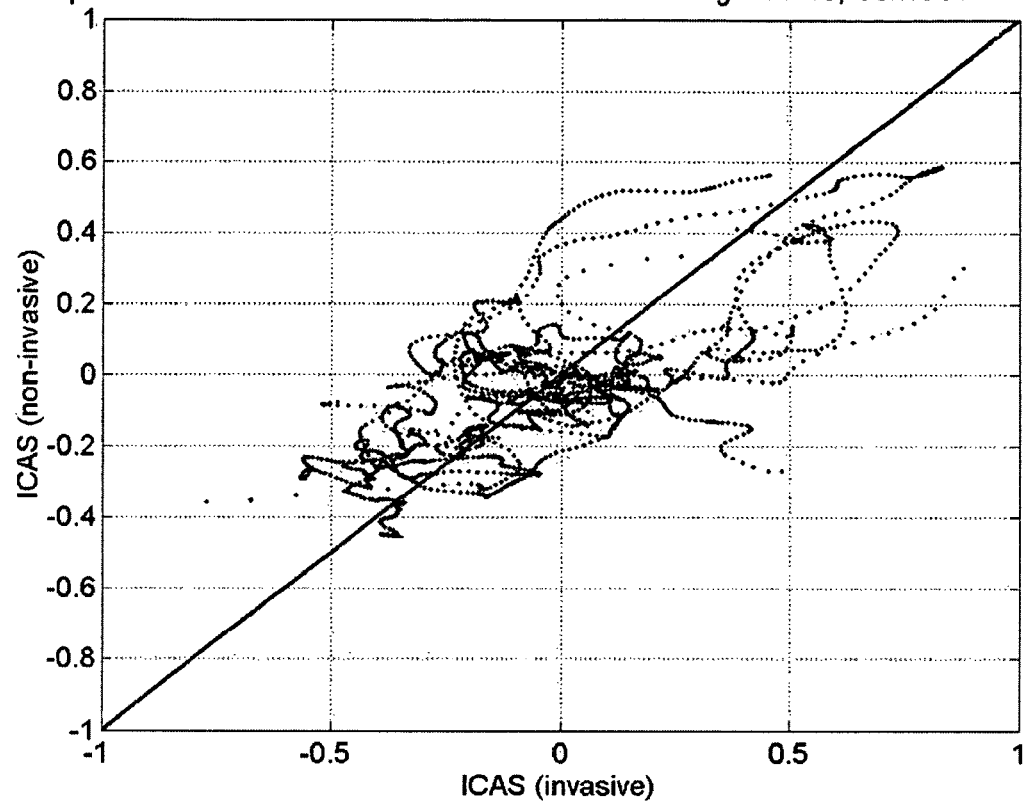
FIG. 4 is a chart showing plot of non-invasive CAS monitoring data versus invasive CAS data. The non-invasive ICAS clinical data was collected and processed using the method of the present invention.

In order to compare the invasive ICAS and non-invasive ICAS data, the data obtained from the seven patients was plotted in FIG. 3. The non-invasive ICAS data was collected using an embodiment of the method 10 and apparatus 11 of the present invention. The data from each patient is marked on the chart. In order to fit a linear relationship between invasive ICAS and non-invasive ICAS to find a correlation factor, these data points were plotted against each other in FIG. 4. The total time of monitoring the seven patients was about 15 hrs. The correlation factor between invasive and non-invasive ICAS data was 0.70933. This evidence demonstrates that the proposed method is suitable for medical application.

The added value of the CAS monitoring method and apparatus disclosed in the present invention is twofold. First, the method does not require the use of additional sensors for the measurement of reference waves, i.e. neither ABP wave, nor lung (respiratory) wave measurement channels. This prevents the introduction of additional phase-shift errors from the apparatus, increases accuracy and reliability, and also reduces the cost of the device.

Figure 5:
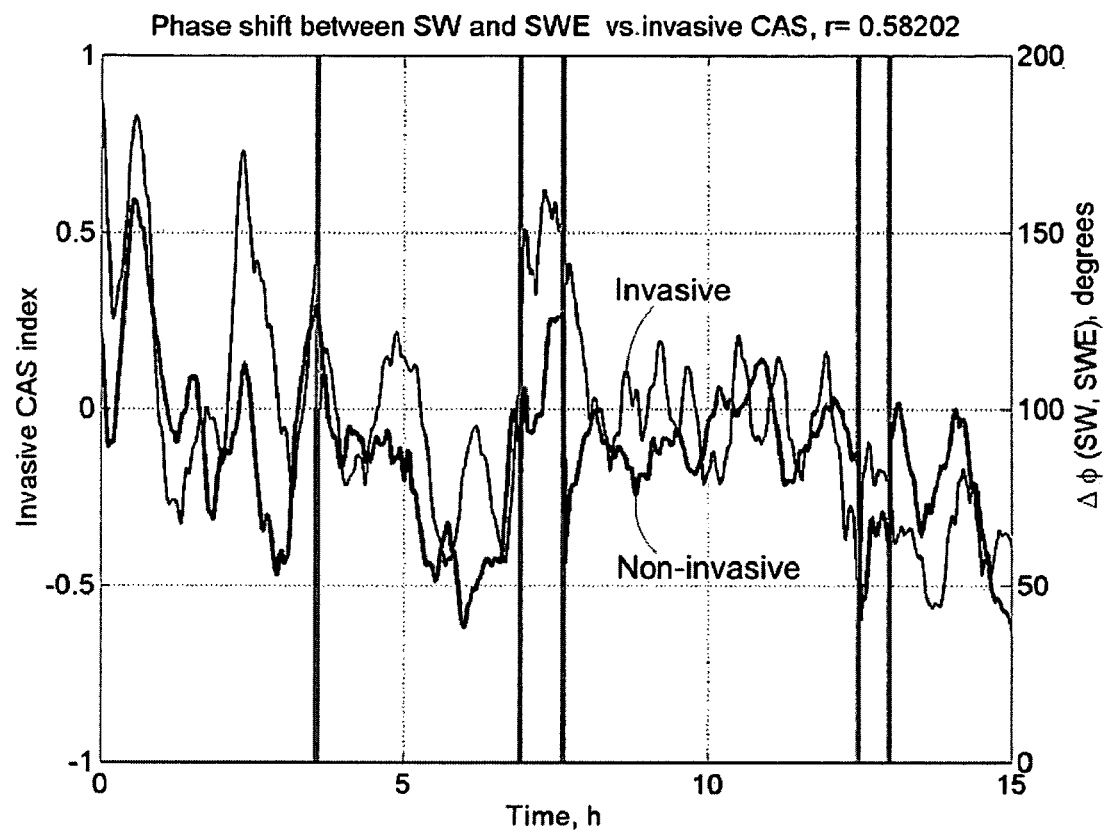
FIG. 5 is a chart showing display results of invasive monitoring data and non-invasive CAS monitoring data represented as a slow wave phase shift $\phi(SW, SWE)$ data. The non-invasive ICAS clinical data was collected and processed using the method of the present invention.
Figure 6:
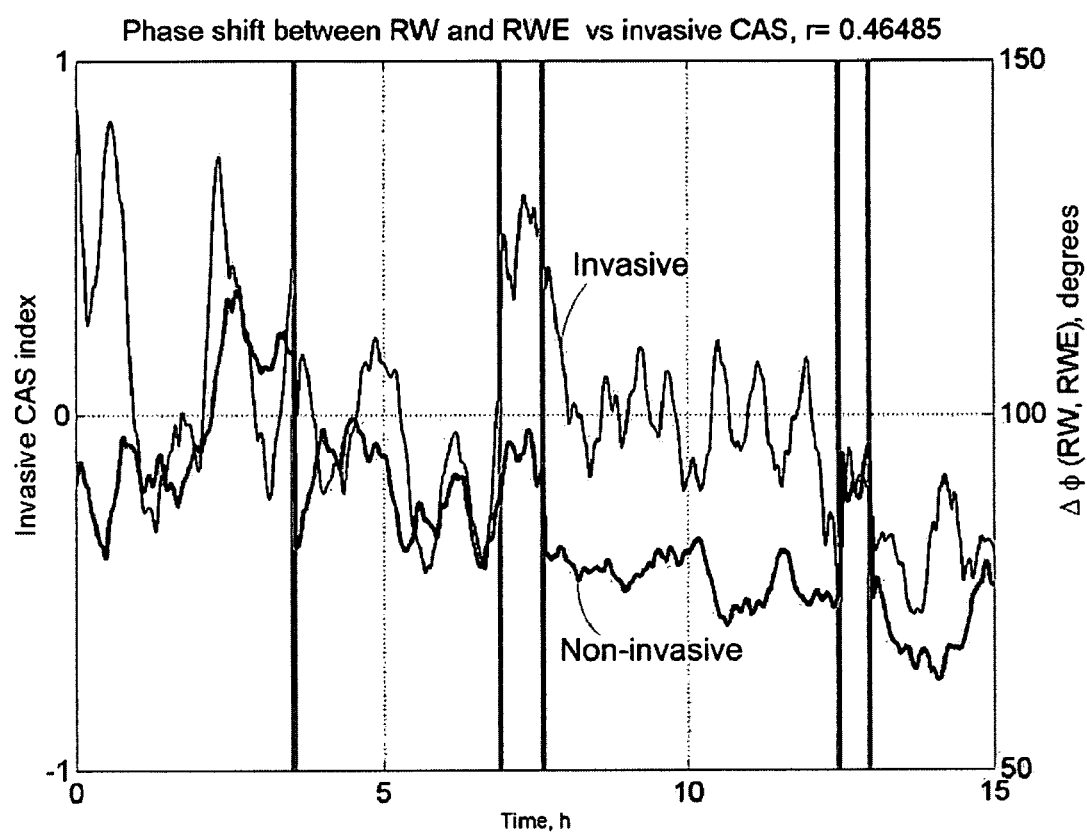
FIG. 6 is a chart showing display results of invasive monitoring data and non-invasive CAS monitoring data represented as a respiratory wave phase shift $\phi(RW, RWE)$ data. The non-invasive ICAS clinical data was collected and processed using the method of the present invention.
Figure 7:
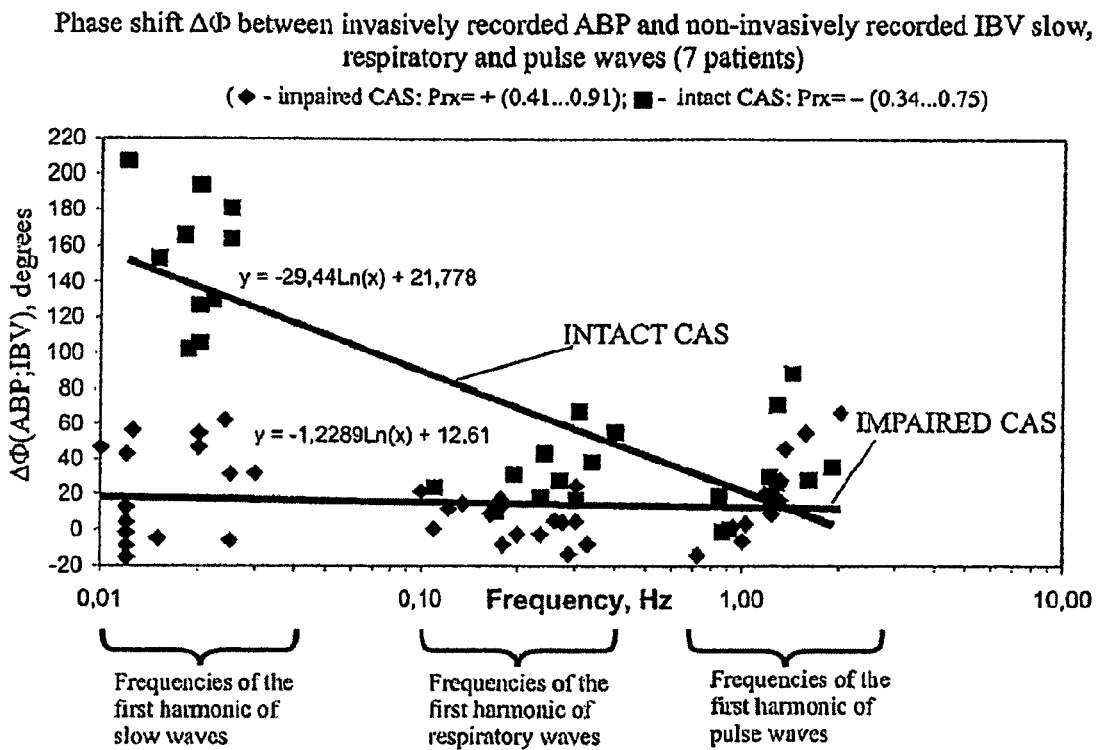
FIG. 7 is a chart showing the phase shift between invasively recorded arterial blood pressure (ABP) and non-invasively recorded intracranial blood volume (IBV) slow, respiratory and pulse waves collected using the method of the present invention.

Second, additional measurement data reliability is obtained by simultaneously measuring both the phase shift between informative slow waves SW and reference slow waves from the envelope SWE, and the phase shift between informative respiratory waves RW and reference respiratory waves from the envelope RWE in order to calculate the CAS index (ICAS). Monitoring only PS1 or PS2 alone is not sufficient to adequately approximate invasively measured ICAS. For example, as shown in FIG. 5, the correlation coefficient between invasive ICAS data and the phase shift PS1=φ(SW, SWE) alone is 0.58202. As shown in FIG. 6, the correlation coefficient between invasive ICAS data and the phase shift PS2=+(RW, RWE) alone is 0.46485. However, by using the combination of PS1 and PS2 data, and after transformation of this data into the index of CAS evaluation, it is possible to increase the quantity of information about CAS. The correlation factor between invasive and non-invasive CAS indexes was increased to 0.70933 (after recalculation of PS1 and PS2 into CAS estimating index: ICAS=f (PS1;PS2).

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method for non-invasively monitoring cerebrovascular autoregulation state comprising the steps of:
    obtaining intracranial blood volume waves;
    filtering a first informative wave from the intracranial blood volume Waves, said first informative wave comprising an intracranial blood volume slow wave;
    filtering a second informative wave from the intracranial blood volume waves, said second informative wave comprising an intracranial blood volume respiratory wave;
    filtering a primary reference wave from the intracranial blood volume waves;
    demodulating the primary reference wave into a reference wave envelope;
    filtering a first reference wave from the reference wave envelope;
    filtering a second reference wave from the reference wave envelope;
    calculating a first phase shift between said first informative wave and said first reference wave;
    calculating a second phase shift between said second informative wave and said second reference wave;
    calculating in a processor an index of evaluation of the status of cerebral autoregulation state from said first phase shift and said second phase shift; and
    comparing in a processor said index of evaluation of the status of cerebral autoregulation state to a predetermined index threshold value to determine cerebrovascular autoregulation state.

2. The method of claim 1 wherein said index of evaluation of the status of cerebral autoregulation state is calculated using the following formula:

$$ICAS=\cos(\pi - a1*PS1 - a2*PS2)$$

wherein PS1 is said first phase shift and PS2 is said second phase shift and where a1 and a2 are weighting factors.

3. The method of claim 2 wherein the value of weighting factor a1 is 0.61 and the value of weighting factor a2 is 0.42.

4. The method of claim 1 wherein said primary reference wave comprises an intracranial blood volume pulse wave.

5. The method of claim 1 wherein said first reference wave comprises a slow wave from the pulse wave envelope.

6. The method of claim 1 wherein said second reference wave comprises a respiratory wave from the pulse wave envelope.

7. The method of claim 1 further comprising the step of determining said cerebrovascular autoregulation state is absolutely intact when said calculated ICAS is close to −1.0.

8. The method of claim 1 further comprising the step of determining said cerebrovascular autoregulation state is absolutely impaired when said calculated ICAS is close to +1.0.

9. A method for non-invasively monitoring cerebrovascular autoregulation state comprising the steps of:
    non-invasively obtaining intracranial blood volume waves;
    filtering a slow wave informative component from said intracranial blood volume waves, said slow wave informative component comprising an intracranial blood volume slow wave;
    filtering a respiratory wave informative component from said intracranial blood volume waves said respiratory wave informative component comprising an intracranial blood volume respiratory wave;
    filtering a pulse wave component from said intracranial blood volume waves;
    demodulating said pulse wave component into a pulse wave envelope;
    filtering a slow wave reference component from the pulse wave envelope;
    filtering a respiratory wave reference component from the pulse wave envelope;
    calculating a first phase shift between said slow wave informative component and said slow wave reference component;
    calculating a second phase shift between said respiratory wave informative component and said respiratory wave reference component;
    calculating in a processor the index of evaluation of the status of cerebral autoregulation state from said first phase shift and said second phase shift; and
    comparing in a processor said index of evaluation of the status of cerebral autoregulation state to a predetermined index threshold value to determine cerebrovascular autoregulation state.

10. The method of claim 9 wherein said index of evaluation of the status of cerebral autoregulation state is calculated using the following formula:

$$ICAS=\cos(\pi - a1*PS1 - a2*PS2)$$

wherein PS1 is said first phase shift and PS2 is said second phase shift and where a1 and a2 are weighting factors.

11. The method of claim 10 wherein the value of weighting factor a1 is 0.61 and the value of weighting factor a2 is 0.42.

12. The method of claim 9 further comprising the step of determining said cerebrovascular autoregulation state is absolutely intact when said calculated ICAS is close to −1.0.

13. The method of claim 9 further comprising the step of determining said cerebrovascular autoregulation state is absolutely impaired when said calculated ICAS is close to +1.0.

14. An apparatus for non-invasively monitoring cerebrovascular autoregulation state comprising:
    a device for obtaining intracranial blood volume waves and generating a blood volume output signal;
    a first slow wave filter connected to said device for receiving the blood volume output signal, filtering the blood volume output signal, and generating a slow wave informative signal from said blood volume output signal, said slow wave informative signal comprising an intracranial blood volume slow wave;
    a first respiratory wave filter connected to said device for receiving the blood volume output signal, filtering the blood volume output signal, and generating a respiratory wave informative signal from said blood volume output signal, said respiratory wave informative signal comprising an intracranial blood volume respiratory wave;

a pulse wave filter connected to said device for receiving the blood volume output signal, filtering the blood volume output signal, and generating a pulse wave reference signal;

an envelope detector connected to said pulse wave filter for receiving said pulse wave reference signal, for demodulating said pulse wave reference signal into a pulse wave envelope, and generating a pulse wave envelope signal;

a second slow wave filter connected to said envelope detector for receiving the pulse wave envelope signal, filtering the pulse wave envelope signal, and generating a slow wave reference signal;

a second respiratory wave filter connected to said envelope detector for receiving the pulse wave envelope signal, filtering the pulse wave envelope signal, and generating a respiratory wave reference signal;

a first phase shift monitor connected to the first slow wave filter for receiving the slow wave informative signal and the second slow wave filter for receiving the slow wave reference signal, determining the phase shift between the slow wave informative signal and the slow wave reference signal, and generating a first phase shift value output;

a second phase shift monitor connected to the first respiratory wave filter for receiving the respiratory wave informative signal and the second respiratory wave filter for receiving the respiratory wave reference signal, determining the phase shift between the respiratory wave informative signal and the respiratory wave reference signal, and generating a second phase shift value output; and a processor for receiving the first phase shift value output from the first phase shift monitor and the second phase shift value output from the second phase shift monitor, calculating an index of evaluation of the status of cerebral autoregulation state, said processor also having a stored predetermined index threshold value, and comparing said index of evaluation of the status of cerebral autoregulation state value with said index threshold value to determine the status of cerebrovascular autoregulation state.

15. The apparatus of claim 14 wherein said device is a non-invasive measurement device.

16. The apparatus of claim 14 wherein said device is an ultrasonic "time-of-flight" measurement device.

17. The apparatus of claim 14 wherein said first slow wave filter and second slow wave filter comprise a bandpass filter having a bandwidth of approximately 0.008 Hz to 0.033 Hz.

18. The apparatus of claim 14 wherein said first respiratory wave filter and said second respiratory wave filter comprises a bandpass filter having a bandwidth of approximately 0.1 Hz to 0.35 Hz.

19. The apparatus of claim 14 wherein said pulse wave filter comprises an adaptive bandpass filter having a bandwidth ranging from approximately the frequency of the first harmonic of the pulse waves to the frequency of the fifth harmonic of the pulse waves.

20. The apparatus of claim 14 wherein said processor calculates the index of evaluation of the status of cerebral autoregulation state from the following formula:

$$ICAS = \cos(\pi - a1 * PS1 - a2 * PS2)$$

wherein PS1 is said first phase shift and PS2 is said second phase shift and where a1 and a2 are weighting factors.

21. The apparatus of claim 20 wherein the value of weighting factor a1 is 0.61 and the value of weighting factor a2 is 0.42.

* * * * *